(12) United States Patent  (10) Patent No.: US 9,161,827 B2
Mansour et al.  (45) Date of Patent: *Oct. 20, 2015

(54) PRE-CHARGED PROPHY ANGLE

(71) Applicant: MERIBEL DENTAL, LLC, Balboa Island, CA (US)

(72) Inventors: George Michel Mansour, Pomona, CA (US); Tim Truitt, Orange, CA (US)

(73) Assignee: MERIBEL DENTAL, LLC, Balboa Island, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/447,289

(22) Filed: Jul. 30, 2014

(65) Prior Publication Data

US 2014/0342307 A1  Nov. 20, 2014

Related U.S. Application Data

(63) Continuation of application No. 13/532,695, filed on Jun. 25, 2012, now Pat. No. 8,821,161, which is a continuation-in-part of application No. 13/331,846, filed on Dec. 20, 2011, now abandoned.

(51) Int. Cl.
*A61C 17/00* (2006.01)
*A61C 17/22* (2006.01)
*A61C 1/08* (2006.01)

(52) U.S. Cl.
CPC ............ *A61C 17/005* (2013.01); *A61C 1/087* (2013.01); *A61C 17/227* (2013.01)

(58) Field of Classification Search
CPC ..... A61C 17/005; A61C 17/227; A61C 1/087
USPC ............ 433/80–90, 102–135, 141–142, 166
See application file for complete search history.

*Primary Examiner* — Edward Moran
(74) *Attorney, Agent, or Firm* — Plager Schack LLP

(57) ABSTRACT

A prophy angle is provided that includes a paste-dispensing assembly that includes an actuator at the proximal end of the housing, and a push rod linked to the actuator and supporting a plunger on the push rod, where the push rod is supported by the housing in a biased manner to permit longitudinal movement within the housing in a reciprocating manner as actuated by the actuator, to dispense a controlled quantity of paste out of the prophy angle.

3 Claims, 13 Drawing Sheets

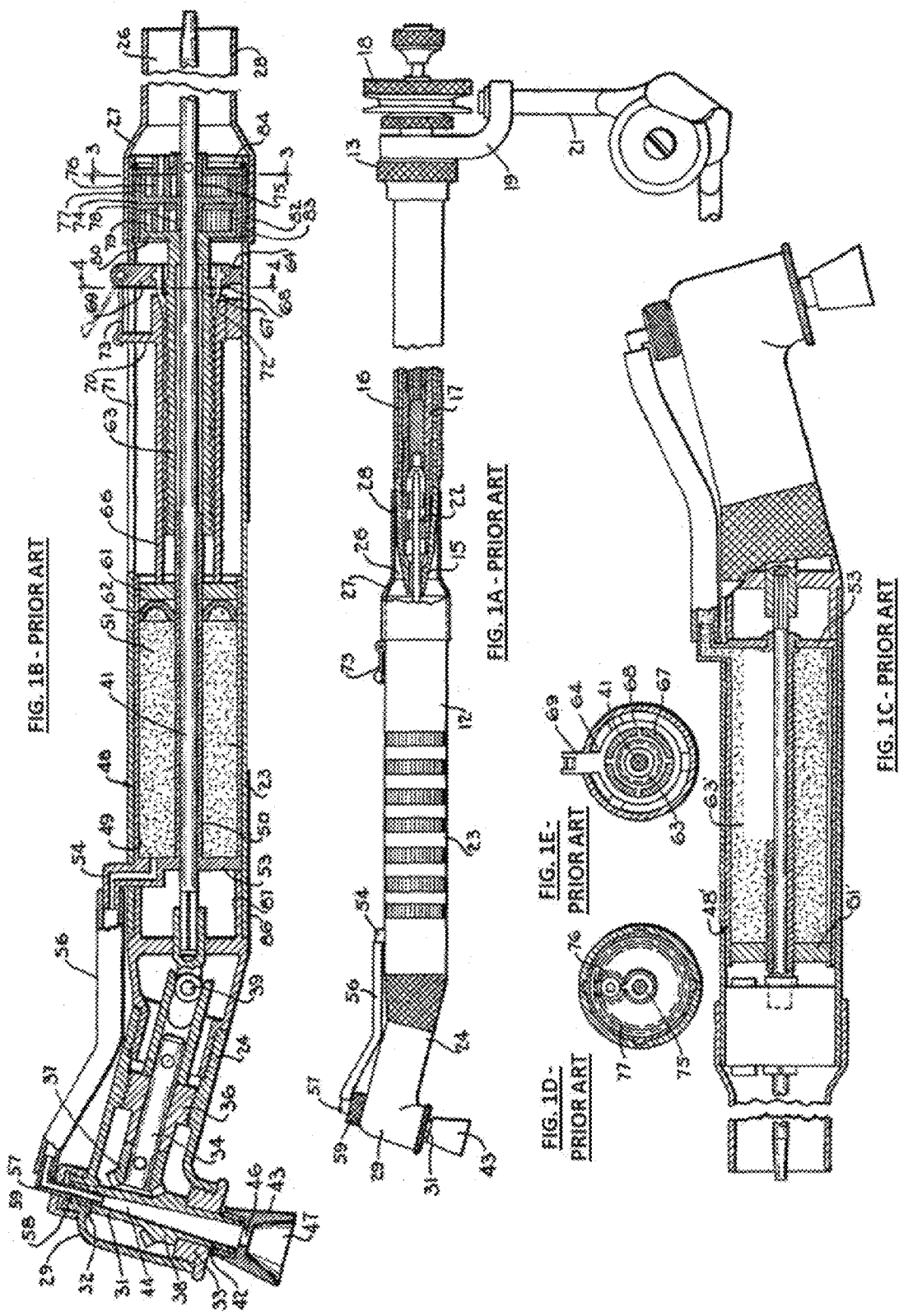

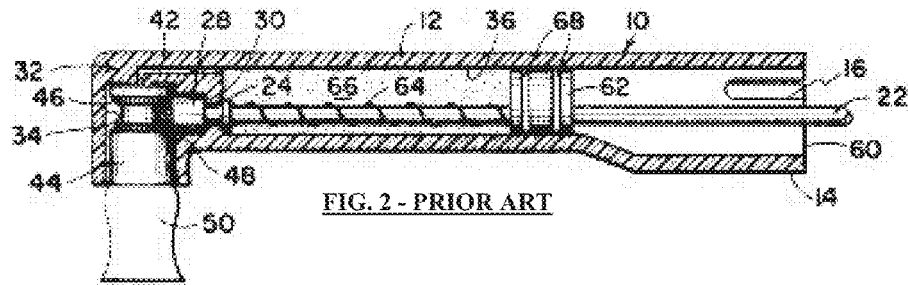
FIG. 2 - PRIOR ART
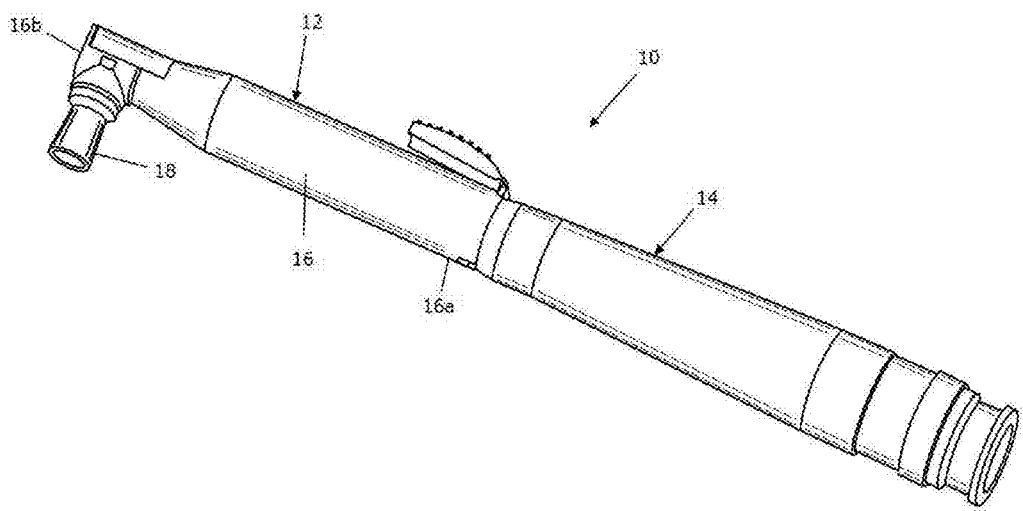
FIG. 3

PRE-CHARGED PROPHY ANGLE

CROSS-REFERENCE TO RELATED APPLICATIONS

This Application is a continuation of U.S. application Ser. No. 13/532,695 filed Jun. 25, 2012, which is a continuation-in-part of U.S. application Ser. No. 13/331,846, filed on Dec. 20, 2011 entitled "Pre-Charged Prophy Angle".

BACKGROUND

The embodiments herein relate generally to a self-contained prophy angle employing an effective delivery system for dispensing dentifrice in a controlled and economical manner.

A prophy angle is a generally small hand-held device used by dental clinicians to apply therapy to a patient, usually in the form of specially formulated prophy paste for teeth polishing. A rotating cup is often detachably affixed to the distal tip of the prophy angle at an angle to the main longitudinal housing of the prophy angle. The proximal end of the prophy angle is configured as a handle so that the dental clinician, such as a dental hygienist, can exert some comfortable force to polish a patient's teeth with prophy paste applied to the cup.

Traditionally, prophy paste is manually applied to the cup prior to its insertion in the mouth, and then the cup applied to the patient's teeth while power is applied to the device to rotate the cup at a fairly high speed. In that regard, the proximal end of the prophy angle comprises a housing with an opening for accepting therewithin, typically via friction fit, a handle containing a drive mechanism. Historically, the drive mechanism was powered by a tethered drive cable, but since then the drive mechanism comprises a pneumatically-driven motor powered by a tethered air hose. The drive motor is conventionally configured to engage a drive shaft extending from the proximal end of the prophy angle. The drive shaft is axially positioned generally centrally within the prophy angle such that, at a distal end of the drive shaft, a set of bevel gears is typically provided that, in turn, rotatably drive the cup positioned at about an angle normal to the drive shaft.

Over the years, numerous configurations of prophy angles have been presented, with many never becoming commercialized. A prophy angle is intended to be a sturdy but generally light-weight device that is intended for single use only in an effort to address certain infection control issues in the dental practice. Certain bells and whistles have been suggested for the prophy angle over time, but one that has value, but has not yet been commercialized, is a pre-charged prophy angle; i.e., a prophy angle containing a chamber for storing prophy paste and means for discharging the paste as needed. In that regard, numerous patents have been issued on the general scheme of a self-contained prophy angle, including U.S. Pat. No. 2,400,912 to Britt et al.; U.S. Pat. No. 3,389,468 to Lewis, U.S. Pat. No. 3,579,835 to Levenson, U.S. Pat. No. 3,769,707 to Condon, U.S. Pat. No. 3,775,849 to Condon, U.S. Pat. No. 3,987,550 to Danne et al., U.S. Pat. No. 4,220,446 to Walker, U.S. Pat. No. 4,266,933 to Warden et al., U.S. Pat. No. 5,062,796 to Rosenberg, U.S. Pat. No. 5,208,933 to Lustig et al., U.S. Pat. No. 5,642,994 to Chipian et al., U.S. Pat. No. 5,871,353 to Pierce et al., U.S. Pat. No. 5,927,976 to Wu, U.S. Pat. No. 6,632,090 to Randolph, U.S. Pat. No. 7,070,412 to Stadeker, U.S. Pat. No. 7,101,182 to Garrison et al., U.S. Pat. No. 7,160,108 to Jaffe, U.S. Patent No. Appl. No. 2009-0098505 to Randolph, and PCT Appl. No. WO2009-140630 to Bellanti. None have been known to be successfully commercialized, ostensibly because they are generally not clinically relevant, not cost effective or commercially viable.

By way of specific example, FIG. 1 herein reflects figures from the '912 patent to Britt et al. The disclosed device includes a means of forcing the paste from a chamber to a recess in the tool, which includes a plunger mounted for reciprocation in the chamber that engages the shell and has formed therein a central opening to accommodate the shaft and the shell therearound. With the chamber filled with paste and the plunger in the retracted position, appropriate forward movement of the plunger forces the paste out through the tube and passages. The mechanism of action, as reflected by the arrangement of components in FIG. 1 herein, however, evidences a level of complexity that makes operation inefficient and terribly cost inefficient to manufacture.

By way of an additional example, FIG. 2 herein reflects a figure from the '468 patent to Lewis. There, a housing is disclosed that is pre-charged with a quantity of paste prior to the insertion of a piston within the housing. Rotation of the drive shaft in a direction for moving the piston toward the shoulder forces the paste within the chamber outwardly through the passageway and through the passageway into the interior chamber of the prophy cup. Simultaneously the rotation of the drive shaft rotates the gear that, in turn, transmits rotation to the cup. Among other limitations, the Lewis device suffers from a lack of control of paste discharge, as the action of discharge is controlled by the system driving rotation of the prophy cup. The other prior art prophy angles, even those containing a pre-charging feature, suffer from similar limitations.

As such, a need has arisen for an effective and cost efficient pre-charged prophy angle to meet the dental treatment needs.

SUMMARY

In that regard, embodiments of the present invention satisfy that need by providing an improved self-contained prophy angle that has independent control over the advancement and discharge of prophy paste or the like while simultaneously controlling rotating of the distal prophy cup or other working tool end. In one embodiment, a hand-held oral hygiene applicator or prophy angle is provided comprising a prophy angle housing having a distal end and a proximal end, where the prophy angle housing is configured to permit the clinician to conveniently handle the prophy angle housing at the proximal end while the distal end is placed within a patient's mouth during use. The prophy angle housing is preferably configured to permit the clinician to simultaneously control the expression of paste while providing the desired treatment to the patient.

In one embodiment, the prophy angle comprises a first drive mechanism positioned within the prophy angle housing comprising a drive shaft for delivering mechanical energy to a rotatable head assembly provided at the distal end of the prophy angle housing; a chamber substantially enclosed within the prophy angle housing, the chamber configured to store paste in a controlled releasable manner, the chamber being configured to permit expression of paste by the clinician from the proximal end of the prophy angle housing; and an independent second drive mechanism provided within the prophy angle housing, the second drive mechanism configured to deliver a controlled amount of paste from the chamber to the distal end of the prophy angle housing for as needed expression thereof to the patient by the clinician, the second drive mechanism comprising an actuator positioned at or proximate the proximal end of the prophy angle housing, an index wheel engaging the actuator so that the wheel may be driven in a stepped rotational manner upon actuation of the actuator by the clinician, the index wheel further engaging a barrel within the reloadable chamber, the barrel axially exerting pressure against the paste within the chamber for delivering a controlled quantity of paste toward the distal end of the prophy angle.

In one embodiment, the secondary drive mechanism comprises a shaft comprising helical thread rotatably supporting the barrel, whereby the chamber and helical thread are sized to deliver a pre-set amount of paste for each actuation of the actuator. In another embodiment, the drive shaft of the first drive mechanism is positioned co-linearly with the helical thread and positioned therewithin. In yet another embodiment, the actuator comprises a finger press comprising a member for engaging the index wheel. If desired, the chamber may be configured to be rechargeable for additional use.

Embodiments of the prophy angle herein comprise a rotatable prophy cup for applying paste to the patient. The prophy cup may have one of several configurations for controlling the flow of paste from within the prophy angle into the prophy cup.

BRIEF DESCRIPTION OF THE FIGURES

The detailed description of some embodiments of the invention will be is made below with reference to the accompanying figures, wherein like numerals represent corresponding parts of the figures.

FIGS. 1A through 1E show prior art figures from U.S. Pat. No. 2,400,912 to Britt et al.;

FIG. 2 shows a prior art figure from U.S. Pat. No. 3,389,468 to Lewis;

FIG. 3 is a schematic perspective view of a first embodiment prophy angle;

DETAILED DESCRIPTION OF CERTAIN EMBODIMENTS

Figure 4:
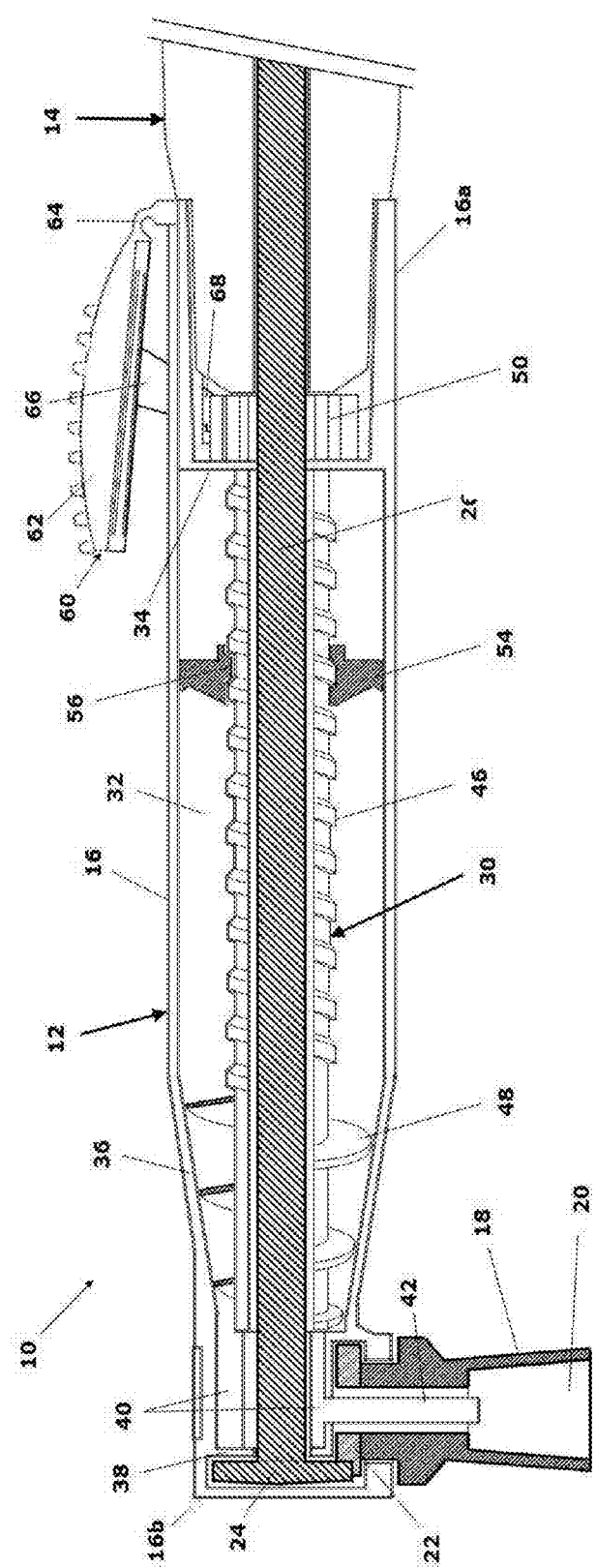
FIG. 4 is a schematic cross-section elevational view of the embodiment of FIG. 3.

By way of example, and referring to FIG. 3, one embodiment of the present invention is a hand-held oral hygiene applicator comprising a self-contained prophy angle 10 comprising a distal member 12 detachably connected to a proximal member 14. The distal member 12 comprises a housing 16 having a proximal end 16a and a distal end 16b supporting a rotatable head assembly or prophy cup 18. The cup 18 may be detachable or fixed to the housing. The proximal member 14 encloses a drive mechanism that is linked directly or indirectly to a power source (not shown). The proximal member 14 further functions to serve as a handle for the dental clinician. The general size and shape may vary from embodiment to embodiment, but it is preferred that the arrangement be such that the prophy angle be configured to permit a user to grasp the proximal member 14 with the hand in a manner to permit an index finger or thumb to be free to exert force upon the distal member 12 for controlled paste expression during use. It is important to note that the invention herein may be used with any type of dentifrice or paste material having therapeutic or non-therapeutic application, depending upon how the dental clinician intends to use embodiments of the invention.

Referring to FIG. 4, the details of the distal member 12 may be appreciated. Provided at the distal end 16b of housing 16 is the prophy cup 18 comprising an internal chamber 20 for discharged paste to accumulate during operation. The prophy cup 18 rotates based upon a drive system, which in one embodiment comprises a first bevel gear 22 engaging a second bevel gear 24 secured to the distal end of a drive shaft 26 that extends axially through the distal member 12. In some embodiments, the drive shaft 26 extends into proximal member 14 by way of friction fit engagement with the drive mechanism (not shown) positioned within the proximal member 14.

In one embodiment, the proximal member 14 is detachably engaged to the distal member 12 via a friction fit, or alternatively within a corresponding connection means within the proximal end 16a of distal member housing 16. In either case, the connection should be made in a manner that the drive mechanism drives the drive shaft 26 so that the prophy cup 18 rotates for dental use. The particulars of the power source and the drive mechanism for the rotating prophy cup are not the subject of the present application. Indeed, one of the benefits of certain embodiments of the present invention is that the drive mechanism for the rotating prophy cup is independent of the self-contained paste-dispensing feature.

In that regard, one embodiment of the present invention comprises a screw shaft 30 rotatably housed within a primary chamber 32 defined at a proximal end by a wall 34 and at the distal end by a tapered portion 36 terminating in a distal wall 38. It should be noted that, although FIG. 4 shows one embodiment generally in elevational cross-section, the screw shaft 30 itself is shown partially in cross-section (above the drive shaft 26) and partially from an external view (below the drive shaft 26) for greater clarity of its configuration in this particular embodiment.

The distal wall 38 partially defines a secondary chamber 40 surrounding the drive shaft 26a in a manner in which the drive shaft is protected from contact with the paste by a surrounding wall. The secondary chamber 40 is fluidly connected to an outlet conduit 42 leading to the dispensing chamber 20 of the prophy cup 18. The secondary chamber 40 and the outlet conduit 42 are configured such that they are not structurally impacted by, and remain stationary during, rotation of the drive shaft and the prophy cup.

The screw shaft 30 comprises an external helical thread 46 positioned along the distal portion of the shaft 30 that is positioned rotatably within primary chamber 32. At the distal portion of the screw shaft 30 is a helical blade 48 that tapers conformingly within the tapered portion 36 of the housing 16. Surrounding the screw shaft is barrel 54 configured to engage the external helical thread 46 of the shaft 30 with a mating internal helical thread 56. With such a configuration, rotation of the screw shaft 30 drives the barrel 54 distally forward in an axial manner; i.e., toward the distal end 16b of the distal member housing 16. The barrel 54 is configured to conform to the internal preferably cylindrical profile of the primary chamber 32 so that any paste stored within the chamber 32 is forced distally (in a quasi stepped plunging action) into the tapered portion 36 of the chamber where the helical blade further drives the paste into the secondary chamber 40 for discharge into the prophy cup chamber 20.

Rotation of the shaft 30 is driven in a controlled fashion by an index wheel or gear 50 that may be indexed radially by manual trigger of dispensing actuation means 60 secured to the proximal housing 16. In one embodiment, the actuation means 60 comprises a finger press 62 preferably ribbed for greater control and rotatably connected to the housing 16 via hinge 64, and is suitable for use with the thumb or index finger. The finger press 62 comprises an extension member 66 that engages at its distal end 68 the gear 50, which preferably has teeth or other indexing means so that depression of the finger press 62 controllably rotates the screw shaft 30 a desired amount. Preferably, the configuration of the prophy angle 10 is designed so that a single indexed radial advancement of the screw shaft by a single finger press corresponds with the discharge of a sensible amount of paste for use by the dental clinician. It need not do so, however, if it would be more desired to express or dispense a smaller or larger quantity for each manual trigger of the actuation means 60.

It is contemplated that the prophy angle 10 be pre-charged with paste during the production process so that it is shipped in a ready-to-use state. For example, the paste may be loaded into the primary chamber 32 prior to placement of the barrel plunger 54 and proximal wall 34 into the proximal end 16a of the distal member housing 16, or through the conduit 42 at the distal end 16b of the housing 16. Or a sealable opening may be provided in the proximal wall 34 or other location within the prophy angle proximal member 12 to permit injection of the paste into the chamber post-production, but prior to shipment. It is even contemplated that the clinician might load the paste into the primary chamber prior to use. The prophy angle may be designed for single use, or multiple use in which appropriate cleaning and/or sterilization methods are employed.

In one embodiment of the present invention, the components of the prophy angle are manufactured using sturdy but light weight materials, including but not limited to lightweight metals, or thermoplastics such as acrylonitrile butadiene styrene (ABS), polypropylene, polyethylene, polycarbonate or sturdy by lightweight material. However, other materials may be used. Indeed, alternative embodiments are contemplated without departing from the spirit of the invention described and claimed herein. Each of the components may be configured differently to accommodate a variety of sizes and arrangements while still maintaining the independence of the discharge of paste from the prophy cup drive mechanism. For example, the distal housing 16 need not include a tapered portion. In another example, the actuation means 60 may comprise a configuration in which the user's finger may engage the gear 50 directly to rotate the screw a set indexed amount. In yet another example, a lock means may be provided to preclude reverse direction of the screw shaft 30. These examples are not intended to be limiting. As such, the invention herein, as reflected by exemplary embodiments presented, should be measured by the claims set forth below.

Figure 5:
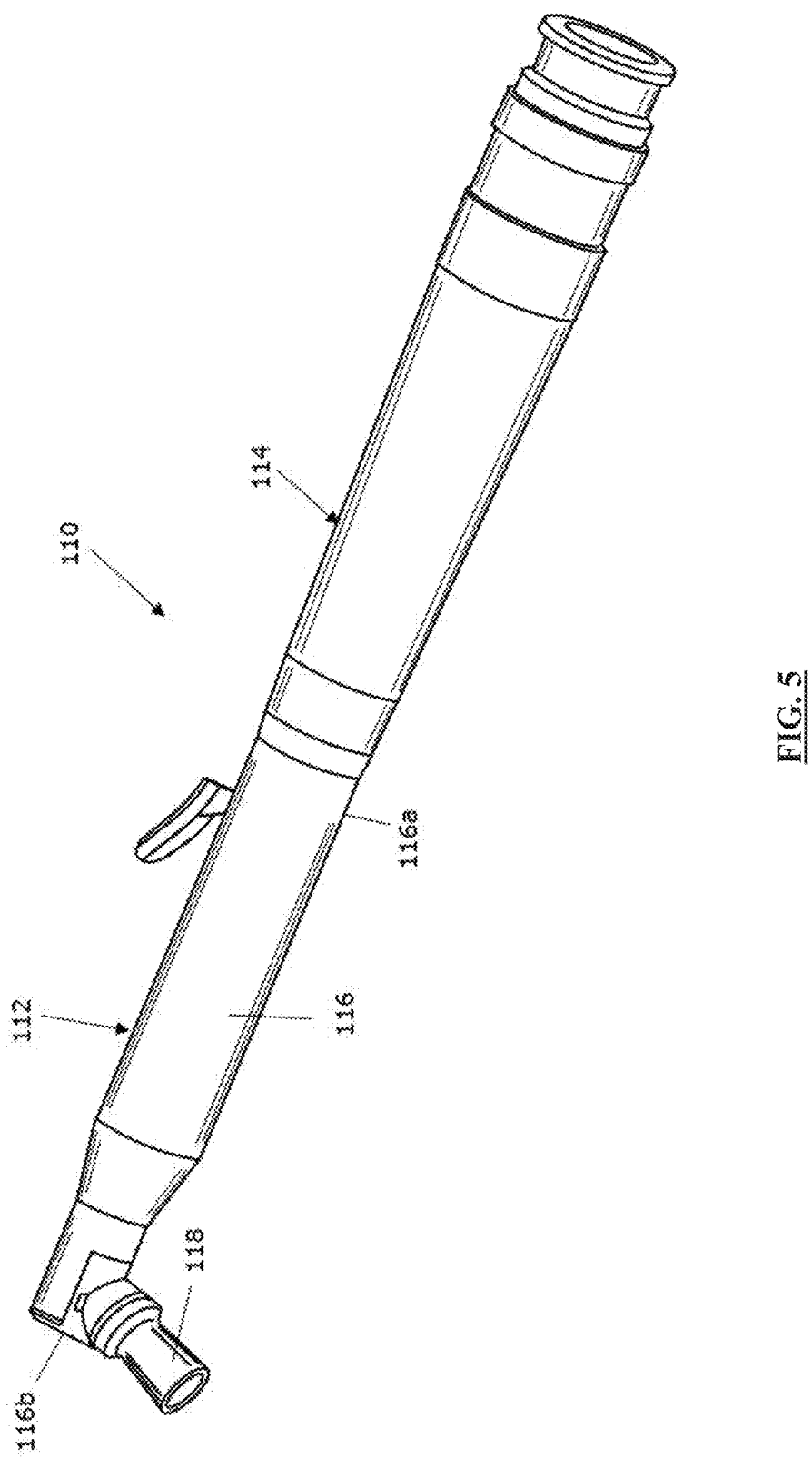
FIG. 5 is a schematic perspective view of a second embodiment prophy angle.

Other embodiments are contemplated for the invention herein. For example, By way of example, and referring to FIG. 5, another embodiment of the present invention is a hand-held oral hygiene applicator comprising a self-contained prophy angle 110 comprising a distal member 112 detachably connected to a proximal member 114. The distal member 112 comprises a housing 116 having a proximal end 116a and a distal end 116b supporting a rotatable head assembly or prophy cup 118. The cup 118 may be detachable or fixed to the housing. As with the other embodiments contemplated or described herein, the proximal member 114 encloses a drive mechanism that is linked directly or indirectly to a power source (not shown), with the proximal member 114 serving as a handle for the dental clinician. Like the other embodiments, the general size and shape may vary from embodiment to embodiment, but it is preferred that the arrangement be such that the prophy angle be configured to permit a user to grasp the proximal member 114 with the hand in a manner to permit an index finger or thumb to be free to exert force upon the distal member 112 for controlled paste expression during use.

Figure 6:
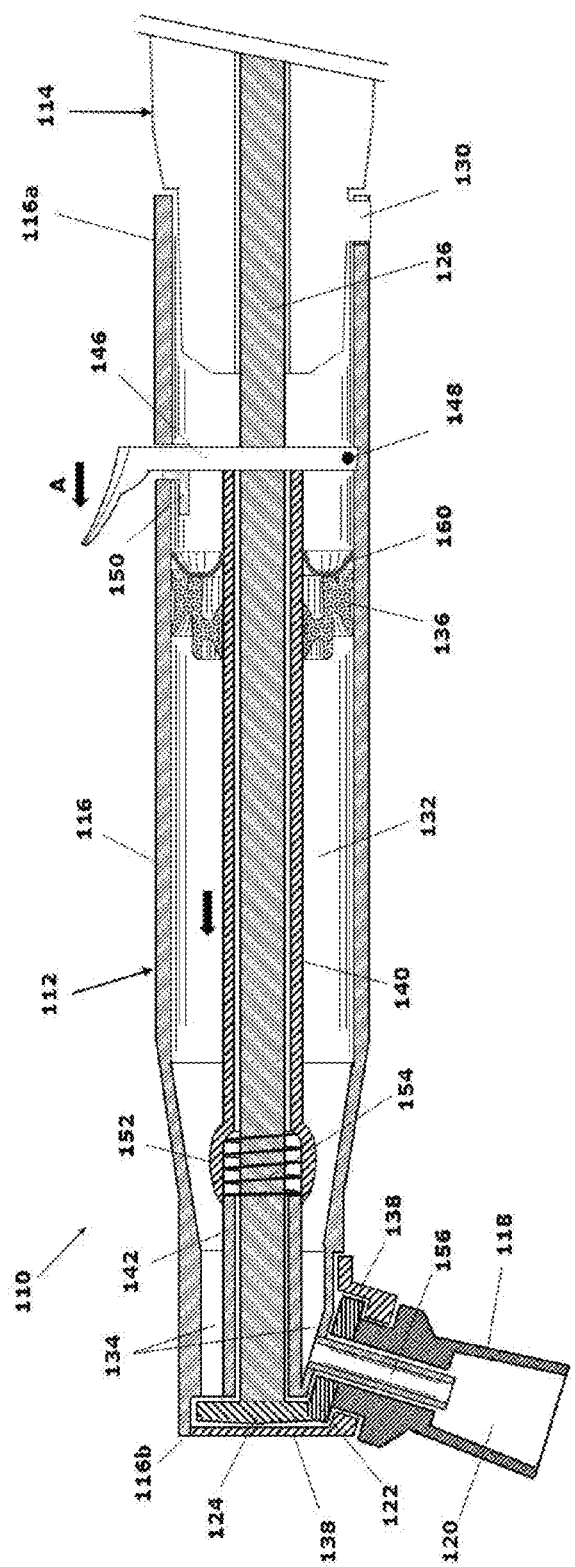
FIG. 6 is a schematic cross-section elevational view of the embodiment of FIG. 5.

Referring to FIG. 6, the details of the distal member 112 may be appreciated. Provided at the distal end 116b of housing 116 is the prophy cup 118 comprising an internal chamber 120 for discharged paste to accumulate during operation. The prophy cup 118 rotates based upon a drive system, which in one embodiment comprises a first bevel gear 122 engaging a second bevel gear 124 secured to the distal end of a drive shaft 126 that extends axially through the distal member 112. In some embodiments, the drive shaft 126 extends into proximal member 114 by way of friction fit engagement with the drive mechanism (not shown) positioned within the proximal member 114.

In one embodiment, the proximal member 114 is detachably engaged to the distal member 112 via a friction fit, or alternatively with a corresponding connection means 130 within the proximal end 116a of distal member housing 116. In either case, the connection should be made in a manner that the drive mechanism drives the drive shaft 126 so that the prophy cup 118 rotates for dental use. As with the other embodiments contemplated herein, the drive mechanism for the rotating prophy cup is independent of the self-contained paste-dispensing assembly. The paste is preferably stored within a chamber 132 defined at the distal end 116b of housing 116 by cavity portion 134 and at the proximal end of housing 116 by a plunger 136 (when at its proximal-most position). A cap fitting 138 may be positioned at the distal end 116b of housing 116 to enclose the first and second bevel gears 122, 124.

The paste-dispensing assembly comprises the plunger 136 that is concentrically supported by a push rod 140 that itself is supported at its distal end by an internal housing tube 142 supported within housing 116. The internal housing tube 142 concentrically supports the distal end of the drive shaft 126 and the second bevel gear, and provides secondary support to the push rod 140. The internal portion 134 of the chamber 132 surrounds the internal housing tube 142 so that when the prophy angle 110 is fully charged, paste fills the primary chamber from the internal portion 134 back to the plunger 136.

Figure 7:
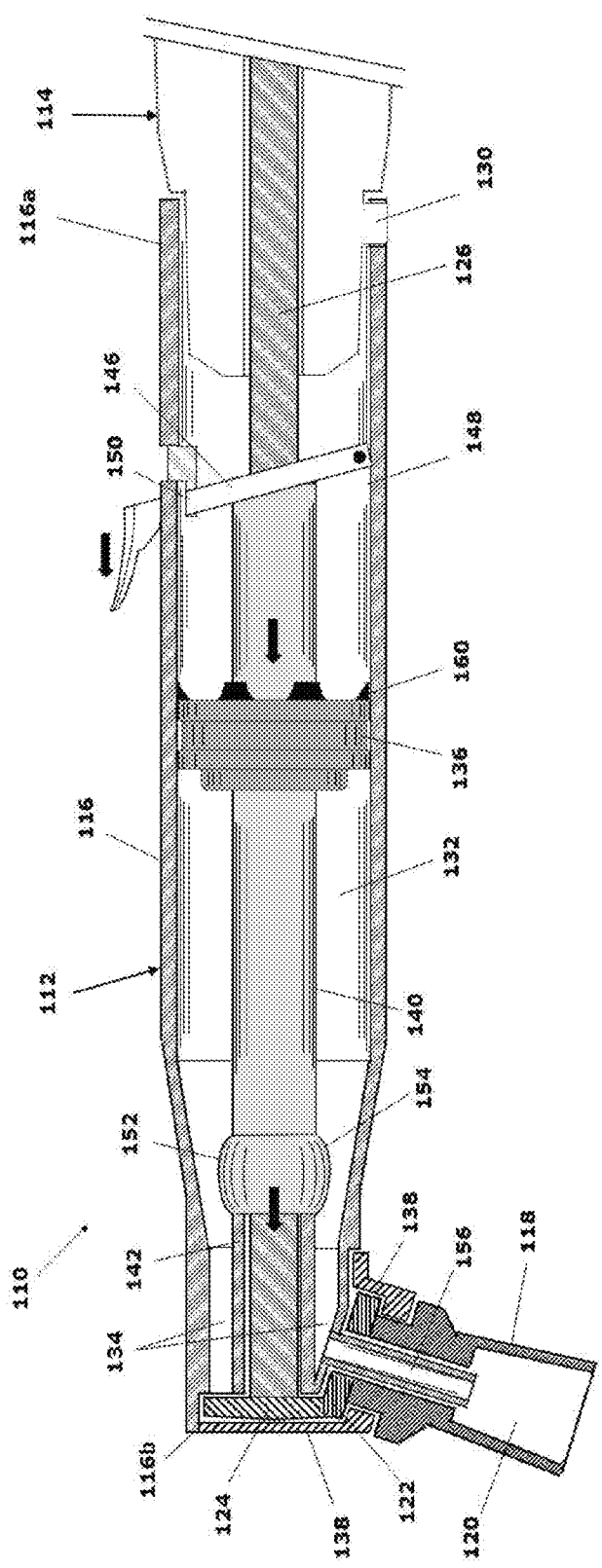
FIG. 7 is a schematic partial cross-sectional view of the embodiment of FIG. 5 during operation.

In one embodiment, the proximal end of the push rod 140 is connected to an actuator, such as a pivotable thumb lever 146 at or proximate the proximal end 116a of the prophy angle housing, which actuator or level is configured to pivot about pivot point 148 secured to the housing 116 or other fixed component therein. The thumb lever 146 may be moved distally (about pivot point 148) in the direction of arrow A within slot 150 of housing 116 so as to push move the push rod 140 distally at the same time, as shown in FIG. 7. A distal tip 152 of the push rod 140 is sized and shaped to concentrically fit about the exterior of internal housing tube 142 and to contain a spring 154 therewithin. As the push rod 140 is moved distally, spring 154 is compressed so that when pressure on the thumb lever 146 is released, the spring exerts counterforce on the push rod to push it proximally, permitting the thumb lever 146 to resume its normal position, as shown in FIG. 6.

The push rod is preferably configured to concentrically house the mid-portion of the drive shaft 126 therewithin. Thus, when charged, the paste housed within chamber 132 encircles the push rod 140 and the internal housing tube 142. The paste in chamber 132 is in fluid communication with external housing tube 156 extending from the distal portion 116b of housing 116. In some embodiments, such as that shown in FIG. 6, the external housing tube 156 extends at an obtuse angle from the longitudinal axis running proximally through the center of the distal member 112 to the proximal member 114, surrounded by fitting 138. The paste stored in chamber 132 may be directed through external housing tube 156 into the cavity 120 of cup 118.

Figure 8:
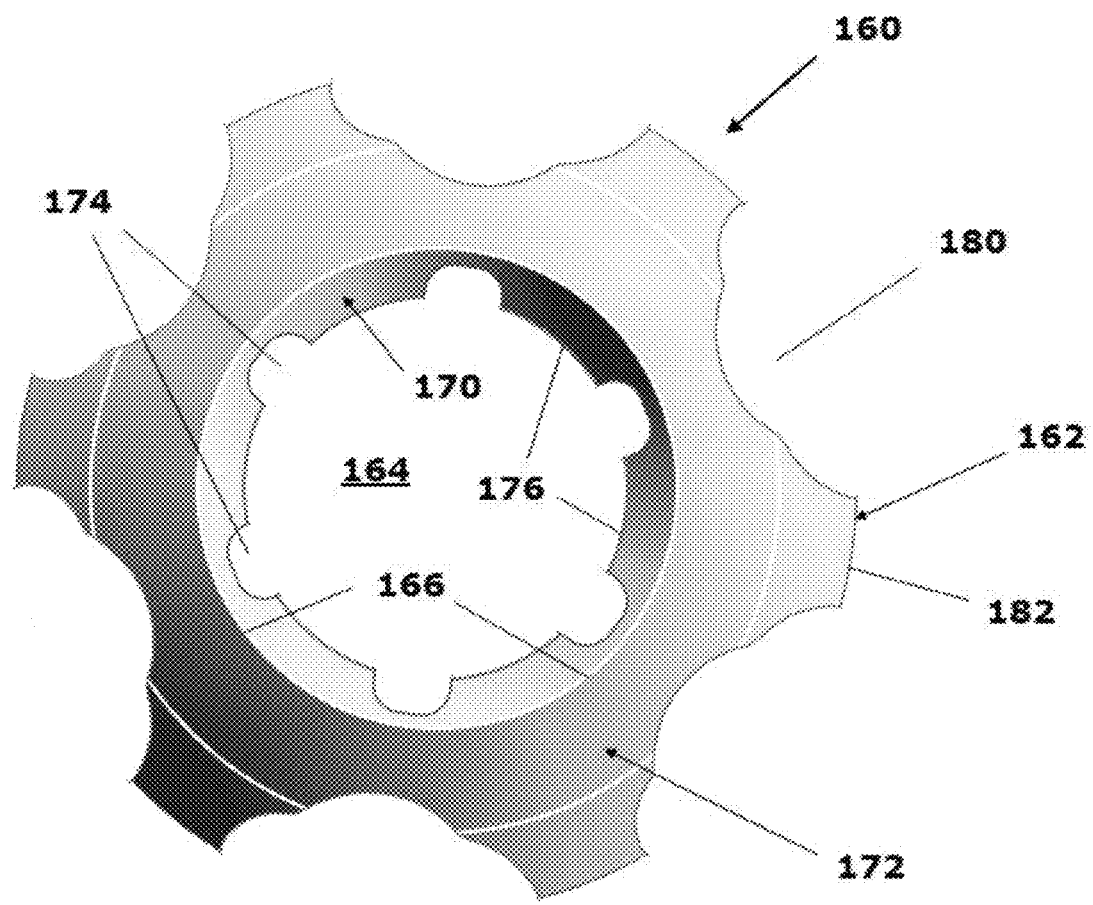
FIG. 8 is a schematic of one embodiment of a plunger retainer.

Still referring to FIGS. 6 and 7, associated with the plunger in at least some embodiments is a plunger retainer 160 comprising a sturdy but resilient material that is configured to move longitudinally in one direction (distally) but resists movement in the opposite direction (proximally). One embodiment of the plunger retainer 160 is shown in greater detail in FIG. 8, and comprises an annular washer-like collar 162 having a central opening 164 therein through which the push rod 140 may extend. The collar 162 of the plunger retainer 160 further comprises preferably an annular apex 166 from which both an inner face 170 and outer face 172 extend in the same direction. For example, as shown in FIG. 8, the annular apex 166 of the embodiment 160 is positioned at the forward junction of the inner and outer faces 170, 172, both of which extend into the paper from there.

Preferably, the inner face 170 comprises a plurality of cut-outs 174 spaced radially about the periphery of the central opening 164 so as to create a plurality of tabs 176. The tabs 176 are preferably sized to frictionally engage the push rod 140 to permit longitudinal movement of the push rod in a proximal direction relative to the plunger retainer 160, but resist longitudinal movement of the push rod in a distal direction. Likewise, the outer face 172 comprises a plurality of cut-outs 180 spaced radially about the outer periphery of the collar 162 so as to create a plurality of tabs 182. The tabs 182 are preferably sized to frictionally engage the interior of housing 116 surrounding chamber 132 to permit longitudinal movement of the plunger retainer 160 in a distal direction relative to the housing 116, but resist longitudinal movement of the plunger retainer 160 in a proximal direction.

Figure 9:
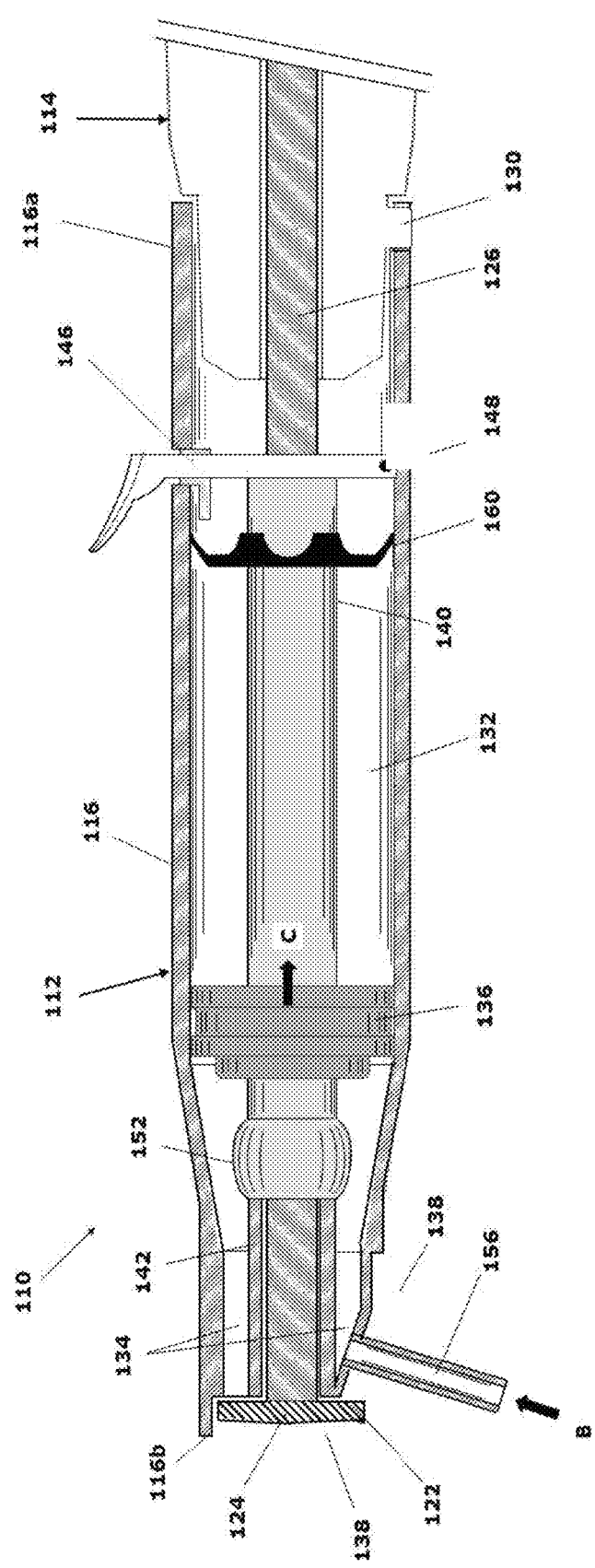
FIG. 9 is a schematic partial cross-sectional view of the embodiment of FIG. 5 during operation.

Referring to FIG. 9, in combination with FIGS. 6 and 7, operation of one embodiment of inventive prophy angle may be described. In that regard, FIG. 9 shows the embodiment 110 with cup 118 removed and plunger 136 in its distal-most position relative to the push rod 140. In this position, a small portion of the paste chamber 132 is distal of the plunger while the larger portion of the chamber 132 is proximal of the plunger. Desirably, a quantity of paste is introduced at the top of external housing tube 156 in the direction of arrow B so that the paste enters into the distal portion of chamber 132 to surround the internal housing tube 142 and the distal portion 152 of push rod 140.

It is contemplated that sufficient paste will be directed into the prophy angle 110 through external housing tube 156 so as to exert proximal-direction pressure against plunger 136 so that the plunger moved proximally in the direction of arrow C, filling the balance of chamber 132 until the plunger is pressed up against the plunger retainer 160 at the proximal end of the push rod 140. As described above, the plunger retainer 160 is configured and sized to resist proximal-direction movement, so that it creates a stop position for the plunger 138, as shown in FIG. 6. At this point, chamber 132 is completely filled with paste, and the prophy angle 110 is essentially "charged" for use. The force of the spring 154 continues to keep the push rod 140 in a proximal-most position until discharge of the paste in the prophy angle 110 is desired.

Referring to FIG. 7, once the prophy cup 118 is put into place, with the first and second bevel gears 122, 124 and cover member 138 in place for operation, the clinician may exert a distal-direction force on the thumb lever 146 to push the plunger 138 and plunger retainer 160 in a distal direction, likewise compressing spring 154. Moving the plunger distally forces paste within chamber 132 to move back out external housing tube 156 into the cavity 120 of prophy cup 118. The prophy angle 110 is preferably designed so that a single full movement of thumb lever 146 through slot 150 of the housing 116 reflects that amount of paste necessary to fill the cavity 120 of cup 118. However, an embodiment of charged prophy angle may be designed so that partial distal movement of the thumb lever is sufficient to fill the cavity or, vice versa, where multiple cycles of thumb lever movement is necessary to fill the cup.

With each distal movement of the thumb lever 146, push rod 140, plunger 138 and plunger retainer 160, the spring 154 is compressed. Upon release of the thumb lever 146, spring 154 will exert sufficient pressure to direct push rod 140 in the proximal direction to replace the thumb lever into its most upright position (its most proximal position). However, due to the configuration of the plunger retainer 160, preferably permitting distal movement relative to the housing 116 but resisting proximal movement relative to the housing 116, the retainer 160 should preclude movement of the plunger 138 in a proximal direction. Only the push rod 140 will move proximally, permitting another cycle (or multiple cycles) of thumb lever depression to express additional quantities of paste as so desired.

Figure 10:
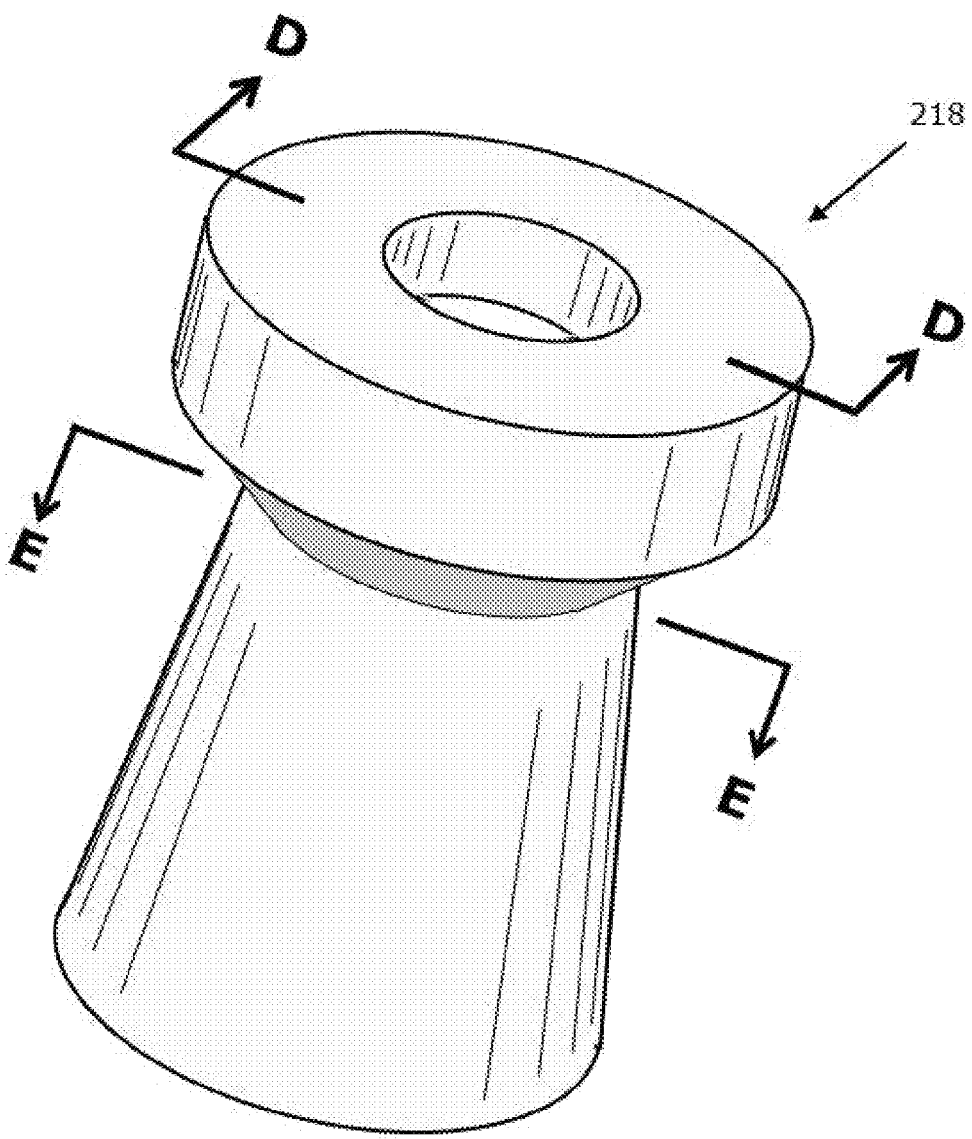
FIG. 10 is a schematic view of an embodiment of a prophy cup to be applied to one or more of the embodiments described herein.

Referring now to FIG. 10, details of embodiments of a prophy cup 118 may be described. In that regard, the embodiment of FIG. 10 is intended to show one example of configuration of a prophy cup, with cross-sectional views D-D and E-E shown in FIGS. 11A through 11D illustrating variations on internal configurations. By way of example, with reference to FIG. 11A specifically, which is a cross-section taken along line D-D of FIG. 10, one embodiment 218 of prophy cup comprises a chamber 220 into which paste may be delivered via any external housing tube (such as 42 and 156 of the prophy angle embodiments described above). Embodiment 218 of prophy cup comprises an internal bore 222 into which external housing tube 42, 156 may be introduced, and further comprises a seal 224, having one of any possible configurations sufficient to fluidly seal the prophy cup about the external housing tube.

Prophy cup 218 may further comprises an outlet 226 into which paste from the housing (of FIGS. 1-9 above) may be dispensed and delivered to chamber 220. The outlet 226 may comprise a simple opening with no obstruction or constriction, or it may comprise one of a number of constrictions or valves to modulate the flow of paste into the cup chamber 220. If desired, the chamber 220 may comprise one or more ribs 228 to facilitate the delivery of paste in an axial direction to the patient.

Figure 11A:
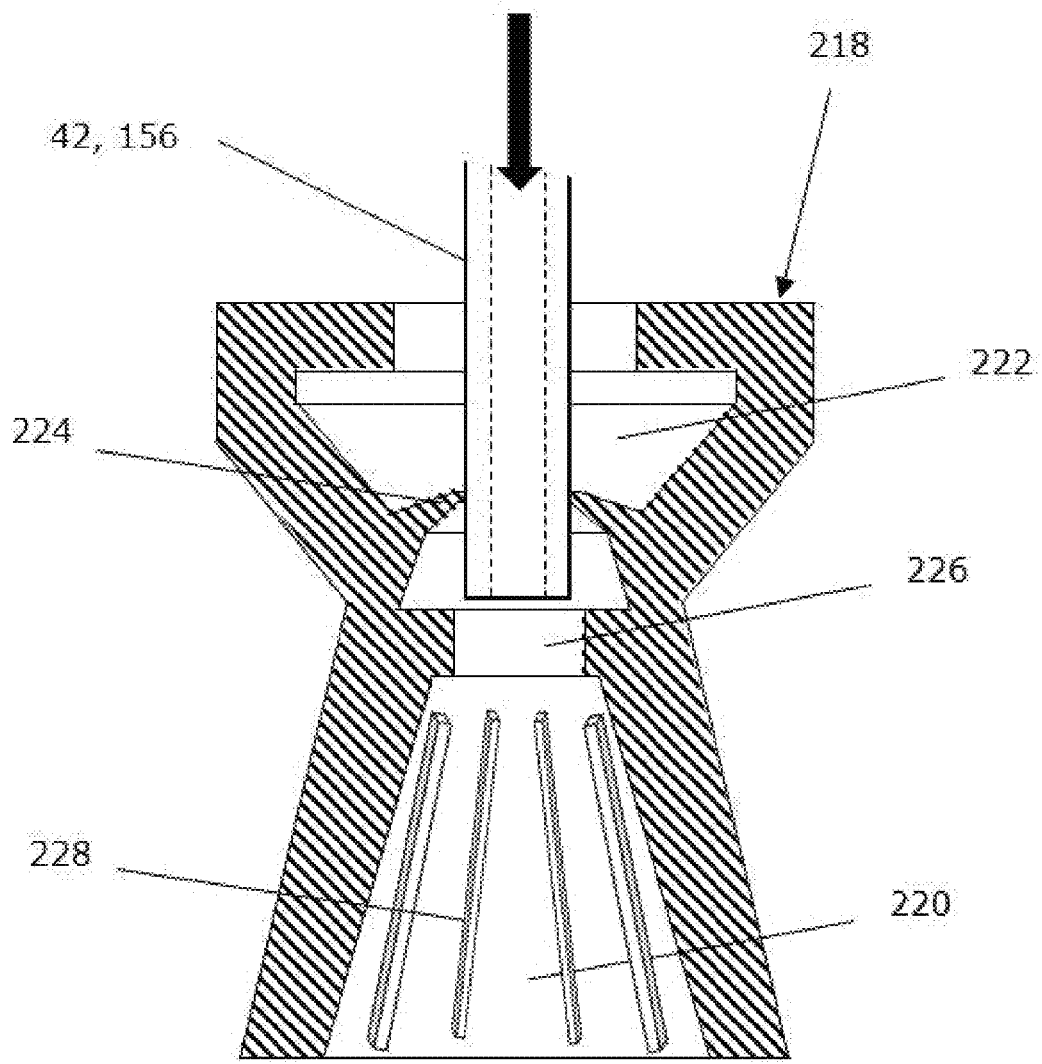
FIG. 11A is a cross sectional view of an embodiment of a prophy cup to be applied to one or more of the prophy angle embodiments described herein.
Figure 11B:
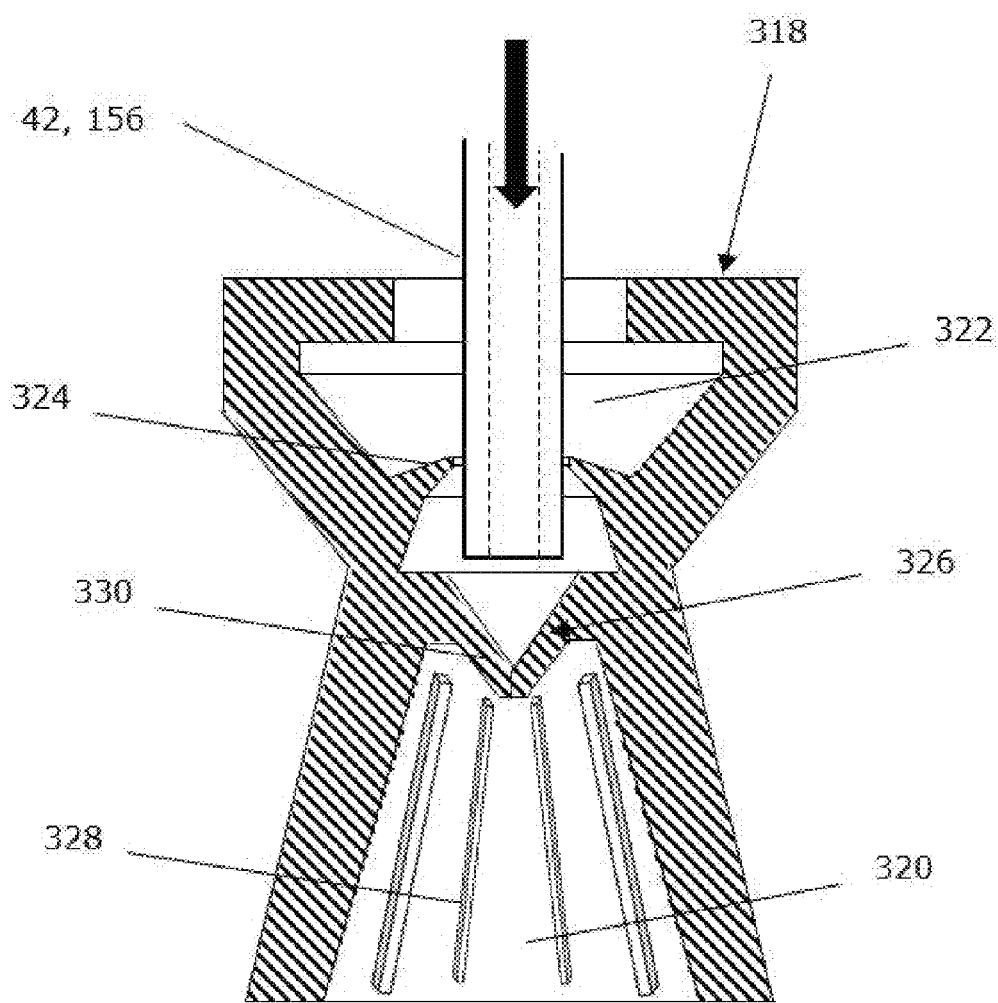
FIGS. 11B and 11C are schematic views of a second embodiment of a prophy cup.
Figure 11C:
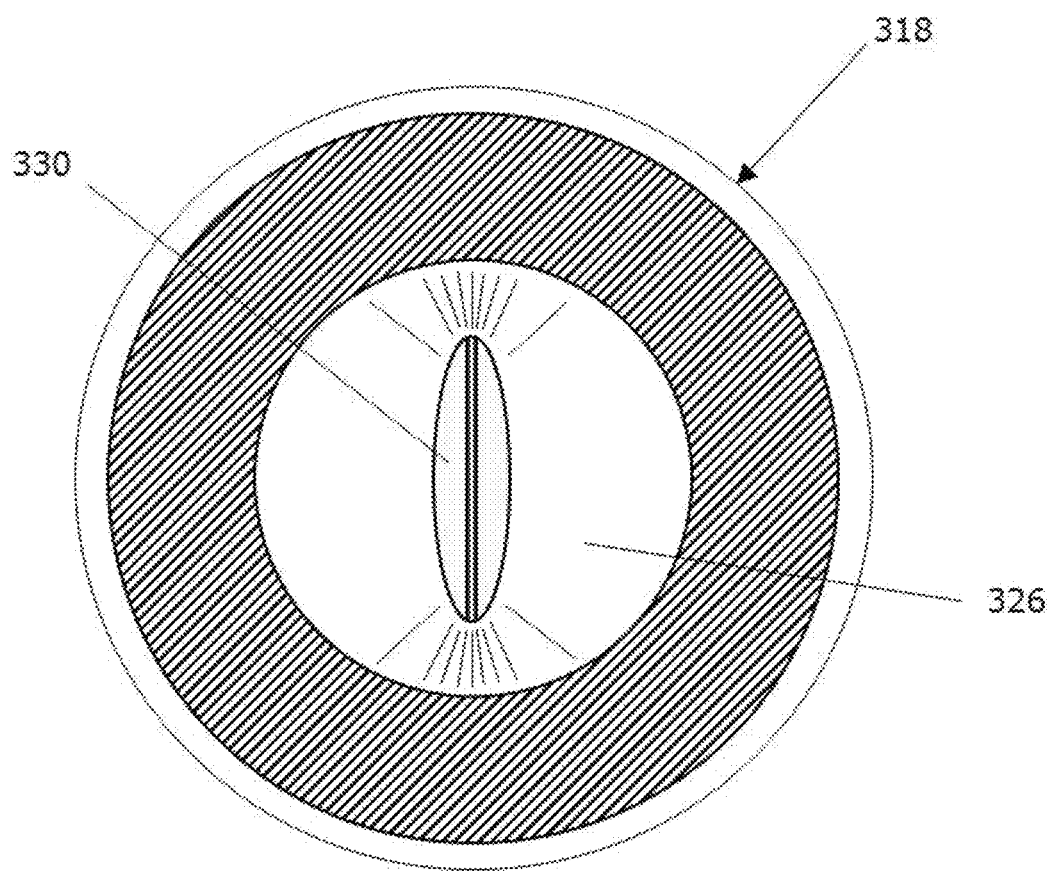

Referring to FIGS. 11B (cross-section taken along line D-D of FIGS. 10) and 11C (cross-section taken along line E-E of FIG. 10), another embodiment of prophy cup 318 may be explained. The cup 318 comprises a chamber 320 and an internal bore 322 into which the external housing tube 42, 156 may be introduced against seal 324. In this particular embodiment, by way of example only, an outlet 326 for the external housing tube 42, 156 comprises a modulated feature, such as a duck bill valve 330. The duck bill valve functions as a check-valve, permitting paste to flow in one direction (toward the patient), but not in a reverse direction. Again, if so desired, cup chamber 320 may comprise ribs 328.

Figure 11D:
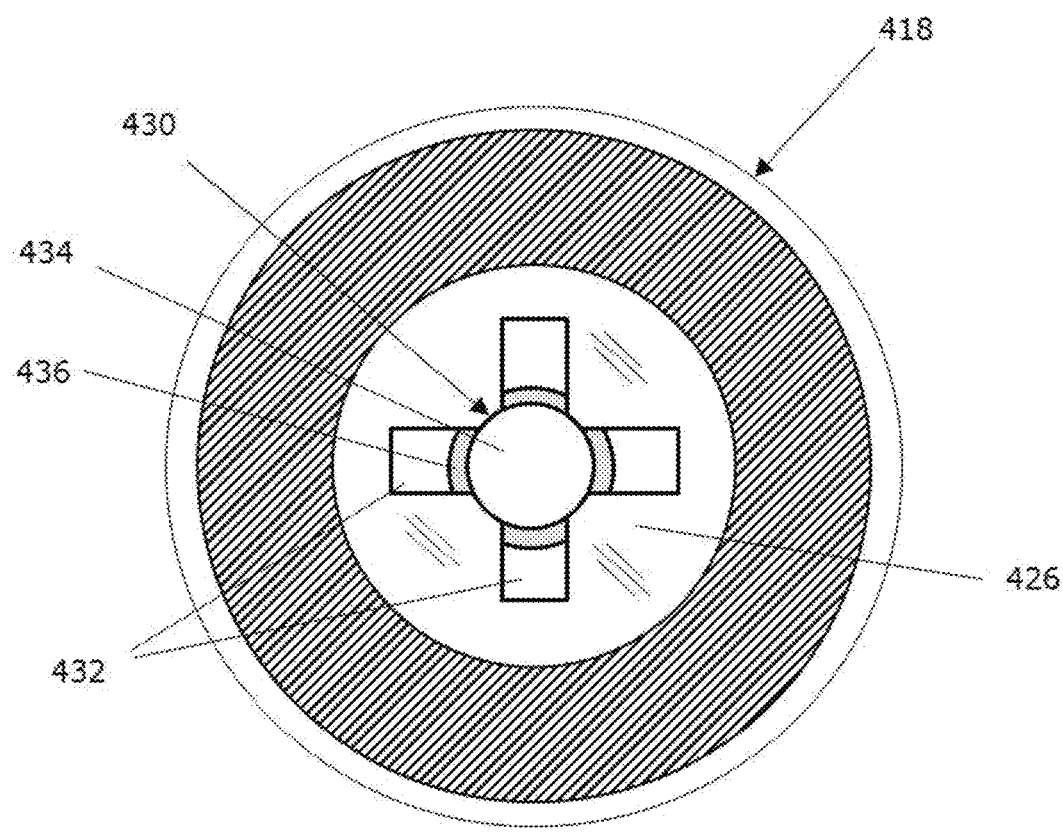
FIG. 11D is a schematic view of a third embodiment of a prophy cup.

In yet another example of an embodiment of a prophy angle cup, FIG. 11D (cross-section taken along line E-E of FIG. 10) illustrates cup 418 comprising an outlet 426 that comprises a construction 430 having a plurality of openings 432 in the construction 430 with a central hub 434 having sloped walls 436 to direct the paste toward the patient yet spread within the cup chamber (not shown). The embodiment of FIG. 11D shows four openings 432 having a generally rectangular configuration, but any number of openings with any number of configurations may be used to facilitate spreading of the paste within the cup chamber.

As with other embodiments described herein, the prophy angle may be precharged during production and shipping to end users, or may be manufactured such that an end user or clinician may charge it prior to use; Other configurations and arrangements are also contemplated that permit independent and controlled expression of paste separate from other operations that may be performed by the prophy angle as driven by the drive shaft. The invention, therefore, is not limited to the particular embodiments described or suggested, but rather is limited by the scope of the claims as presented an issued below.

What is claimed is:

1. A prophy angle comprising:
   a housing that includes a paste chamber,
   a drive mechanism comprising a drive shaft configured for delivering mechanical energy to a rotatable head assembly provided at a distal end of the prophy angle housing, wherein the prophy angle also includes a housing tube configured to fit about at least a portion of the drive shaft of the drive mechanism; and
   a paste dispensing assembly within the housing, the paste dispensing assembly further comprising:
      a push rod arranged on at least a portion of the drive shaft of the drive mechanism and said housing tube, wherein when the housing tube and pushrod are joined together in mechanical engagement, contact between the drive shaft and paste that may be stored within the chamber of the prophy angle housing is precluded in order to maintain effective functioning of the drive mechanism in the presence of paste; the push rod further comprising a distal tip at least partially overlapping a proximal end of the housing tube;
      a spring arranged within the distal tip of the push rod and abutting the proximal end of the housing tube, wherein the spring is configured to permit reciprocal movement of the pushrod linearly relative to the housing tube, wherein reciprocal movement of the pushrod is caused by a user-controlled actuator positioned at a proximal end of the pushrod; and
      a generally cylindrical plunger positioned on at least a portion of the push rod between the actuator and the spring, the plunger comprising an opening therein to permit passage of the push rod there through when in use, the plunger comprising a generally cylindrical seal comprising resilient but sturdy material to pressurize and push the paste contents within the chamber in a distal direction while resisting the passage of pressurized paste between the seal and an interior wall of the prophy angle housing and between the seal and the pushrod when the paste dispensing assembly is in use in the prophy angle, the plunger further comprising a generally cylindrical retainer clip secured to the generally cylindrical seal to preclude proximal movement of the plunger when the actuator is released by the user during use;
   whereby movement of the actuator causes distal movement of the push rod and the generally cylindrical plunger to direct paste in a distal direction when in use in the prophy angle, and whereby release of the actuator causes proximal movement of the pushrod by the spring, but not the generally cylindrical plunger, such that continued actuation of the actuator caused controlled quantities of paste to be delivered out of the prophy angle.

2. The prophy angle of claim 1, further comprising a prophy cup wherein the prophy cup comprises a valve for modulating the flow of paste into the prophy cup during use.

3. The prophy angle of claim 2, wherein the prophy cup comprises a constriction for spreading the flow of paste into the prophy cup.

\* \* \* \* \*